United States Patent [19]
Mongeon

[11] Patent Number: 6,135,111
[45] Date of Patent: Oct. 24, 2000

[54] TRACHEOSTOMY TUBE WITH REMOVABLE INNER CANNULA

[75] Inventor: Douglas R. Mongeon, Orange, Calif.

[73] Assignee: Vital Signs Inc., Totowa, N.J.

[21] Appl. No.: 09/143,792

[22] Filed: Aug. 31, 1998

[51] Int. Cl.[7] ............................................. A61M 16/00
[52] U.S. Cl. ........................... 128/207.15; 128/207.14; 128/200.21
[58] Field of Search ................ 128/200.26, 207.14, 128/207.15, 207.16, 207.17, 207.18, 207.29, 912; 604/264, 523, 524, 530, 531, 525

[56] References Cited

U.S. PATENT DOCUMENTS

| | | | |
|---|---|---|---|
| 3,169,529 | 2/1965 | Koenig | 128/207.15 |
| 3,384,087 | 5/1968 | Brummelkamp | 128/207.15 |
| 3,684,605 | 8/1972 | Zwart | 604/527 |
| 4,304,228 | 12/1981 | Depel | 128/200.26 |
| 4,315,505 | 2/1982 | Crandall et al. | 128/200.26 |
| 4,459,984 | 7/1984 | Liegner | 128/207.15 |
| 4,596,563 | 6/1986 | Pande | 604/264 |
| 4,850,371 | 7/1989 | Broadhurst et al. | 128/207.14 |
| 4,852,565 | 8/1989 | Eisele | 128/207.14 |
| 4,966,141 | 10/1990 | Bacaner et al. | 128/207.14 |
| 5,042,476 | 8/1991 | Smith | 128/207.14 |
| 5,062,420 | 11/1991 | Levine | 128/204.18 |
| 5,067,496 | 11/1991 | Eisele | 128/207.15 |
| 5,119,811 | 6/1992 | Inglis et al. | 128/207.14 |
| 5,199,427 | 4/1993 | Strickland | 128/207.14 |
| 5,308,342 | 5/1994 | Sepetka et al. | 604/282 |
| 5,311,864 | 5/1994 | Huerta | 128/207.15 |
| 5,419,314 | 5/1995 | Christopher | 128/200.26 |
| 5,501,215 | 3/1996 | Huerta | 128/207.15 |
| 5,579,762 | 12/1996 | Lee | 128/207.14 |
| 5,676,659 | 10/1997 | McGurk | 604/282 |
| 5,749,849 | 5/1998 | Engelson | 604/53 |
| 5,819,723 | 10/1998 | Joseph | 128/207.14 |
| 5,957,978 | 9/1999 | Blom | 623/9 |
| 6,062,223 | 5/2000 | Palazzo et al. | 128/207.15 |

FOREIGN PATENT DOCUMENTS

WO 95/23624  9/1995  WIPO ............................ 128/207.15

Primary Examiner—John G. Weiss
Assistant Examiner—Joseph F. Weiss, Jr.
Attorney, Agent, or Firm—R. Gale Rhodes, Jr.

[57] ABSTRACT

A composite tracheostomy tube or cannula comprising a rigid inner tube and a relatively soft outer tube. One or more ducts or chambers are formed between the outer surface of the inner tube and the inner surface of the outer tube. A sealing or mounting flange is attached to the composite tube adjacent one thereof. A balloon or inflatable cuff is attached to the outer surface of the outer tube adjacent the opposite end of the composite tube. A conduit for connection to a fluid source is provided to selectively inflate and/or deflate the inflatable cuff. An inner tube or cannula is removably inserted into the tracheostomy tube. The inner cannula includes a preferred gripping device at the proximal end thereof.

20 Claims, 4 Drawing Sheets

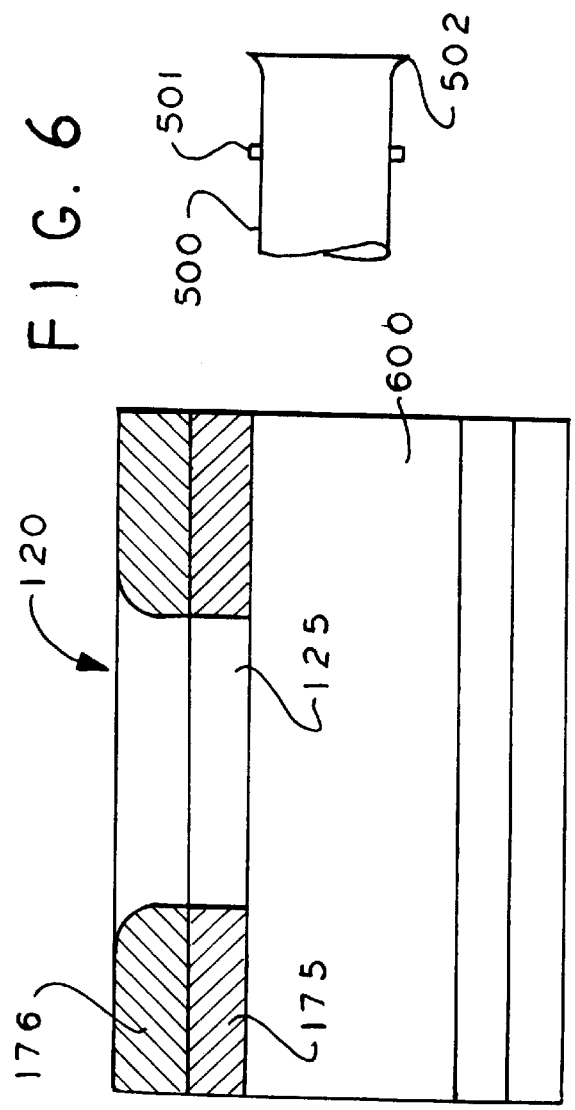
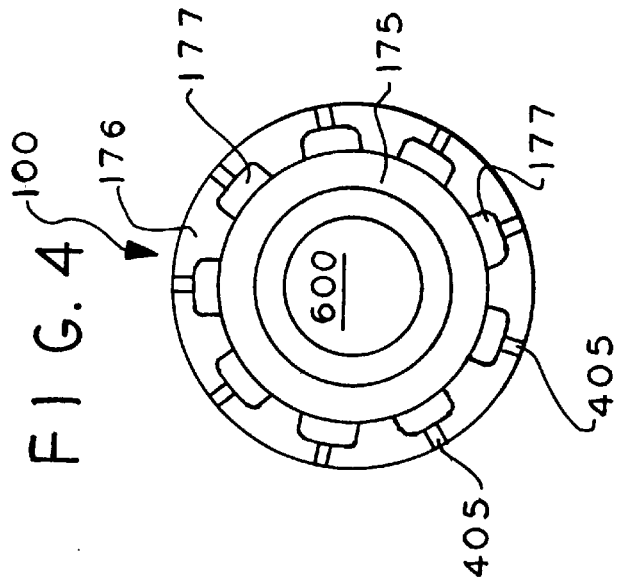
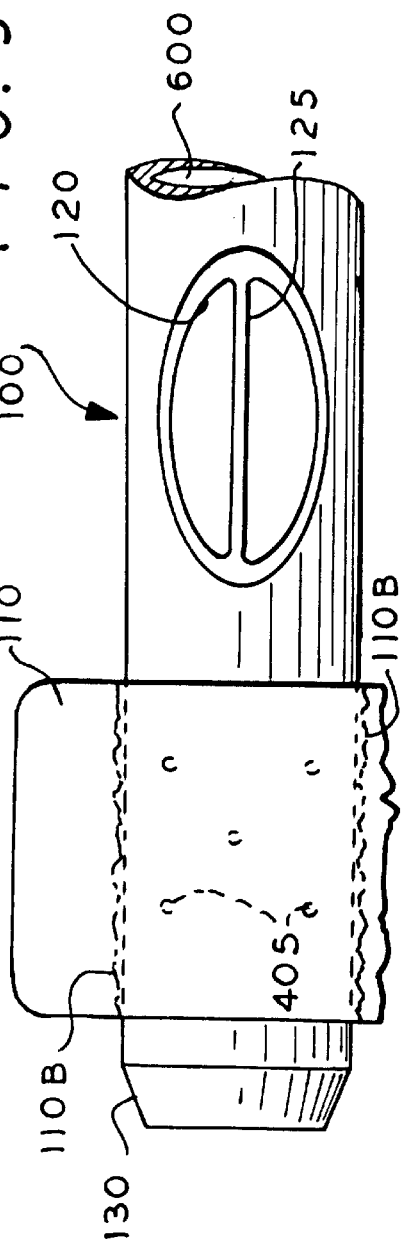

TRACHEOSTOMY TUBE WITH REMOVABLE INNER CANNULA

BACKGROUND

1. Field of the Invention

The present invention relates to respiratory circuits, in general, and, more particularly, to tracheostomy tubes comprising a composite outer cannula and a removable inner cannula.

2. Prior Art Statement

Tracheostomy tubes are well-known in the art. It is also well-known that a two part tracheostomy tube is used so that if the tracheostomy should be occluded by mucous or phlegm, the tracheostomy tube airway can be cleaned by removing the inner cannula, see U.S. Pat. No. 4,817,598, to D. LaBombard, for example.

In the past, the tracheostomy tube has been made of a relatively rigid plastic material such as ABS plastic or the like. These tubes are made according to ASTM or ISO standards which are well-known in the industry. The existing tracheostomy tubes comprise a bent or arcuate tube with a 15 millimeter (or similar) connection at one end which is connected to a breathing circuit or the like. These tubes include flanges at the proximal end thereof for attachment to a neck strap or the like to fasten the tracheostomy tube to the patient.

An inflatable cuff adjacent the distal end of the tube is used to effectively anchor the tracheostomy tube in the patient once the tube has been inserted. That is, the cuff is inflated and prevents removal of the tube from the tracheostomy. (It should be noted that pediatric tracheostomy tubes may not include the cuff for several reasons, notably the size of the patient and the patient's throat.)

The known tracheostomy tubes have several disadvantages. Because of the rigidity of the tube and the hardness of the material, trauma to the patient is frequently inflicted when the tube is inserted into the trachea. In like fashion, the fenestrations or openings in the upper surface of the tube cause trauma to the trachea, as well, because of the sharp edges created by probing the fenestration.

The inflation tube used for inflating the cuff is sometimes mounted in a groove in the cannula. Alternatively, the inflation tube takes the form of a secondary liner externally mounted on the cannula. These additional features also tend to cause trauma to the patient during the insertion and/or manipulation of the tracheostomy tube.

Consequently, improvements in the fabrication and the structure of the tracheostomy tube, in general, are desirable.

SUMMARY OF THE INSTANT INVENTION

A tracheostomy tube or cannula comprising a rigid inner tube and a relatively soft outer tube. At least one duct or chamber is formed between the outer surface of the inner tube and the inner surface of the outer tube. These ducts are, typically, formed on the inner surface of the outer tube. A seating or mounting flange is attached to the composite tube adjacent one end thereof. A balloon or inflatable cuff is attached to the outer surface of the outer tube adjacent the opposite end of the composite tube. The duct (or ducts) communicates with the inner surface of the cuff. A conduit for connection to a fluid source is connected through the mounting flange and communicates with ducts to selectively inflate and/or deflate the cuff. A second tube or cannula is removably inserted into the tracheostomy cannula (tube). A rotatable connector can be used at the proximal end of the tracheostomy tube.

BRIEF DESCRIPTION OF THE DRAWINGS

FIG. 4 is a cross-sectional view of the tracheostomy tube of the instant invention taken along the lines 4—4 in FIG. 3.

FIG. 5 is an enlarged plan view of a portion of the composite tracheostomy tube which shows a fenestration therein.

FIG. 6 is an enlarged cross-sectional view of a portion of the tracheostomy tube shown in FIG. 5 except rotated approximately 90°.

DESCRIPTION OF A PREFERRED EMBODIMENT

Figure 1:
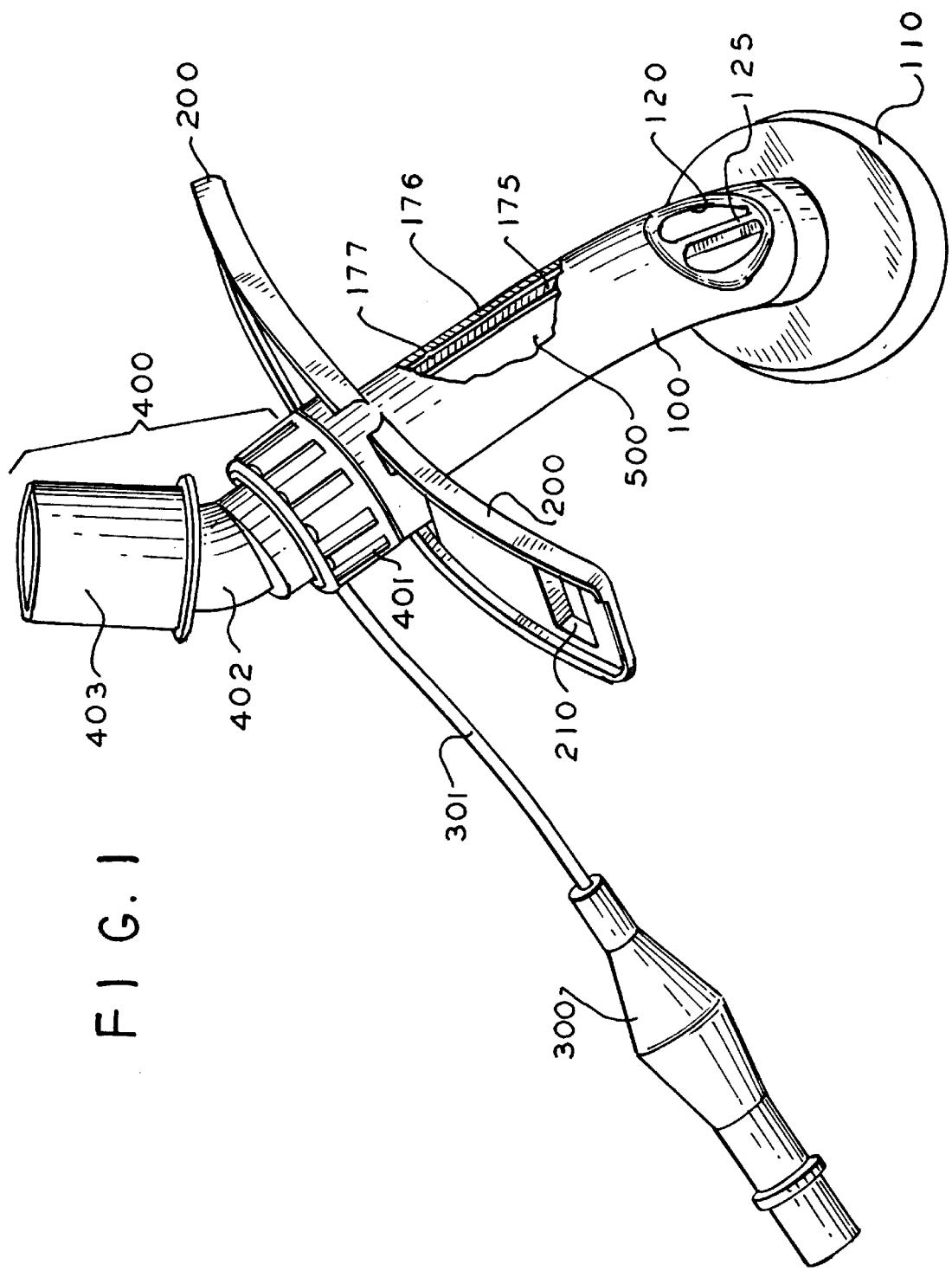
FIG. 1 is a partially broken away, oblique view of a tracheostomy tube in accordance with the instant invention including a rotatable angled connector.

Referring now to FIG. 1, there is shown a partially broken away, oblique view of one embodiment of a composite tracheostomy tube also referred to as a composite tracheal tube (or simply a composite tube) fabricated in accordance with the instant invention. In this embodiment, the tube 100 is an arcuate shaped device of conventional configuration. However, the tube 100 is a composite tube with a rigid inner tube 175 and a relatively soft outer tube 176. Ducts or channels 177 are formed between the inner and outer tubes 175 and 176, as described in greater detail infra.

The arcuate composite tube includes an inflatable balloon or cuff 110 adjacent one end shown in the inflated status. Obviously, when the cuff 110 is not inflated, it is substantially coplanar with the outer surface of the tracheal tube 100.

The tracheal tube 100 includes one or more openings 120 also known as fenestrations. The fenestrations pass completely through the wall of the tube 100 and can be used for non-assisted breathing by the patient when appropriate. The fenestration 120 can be positioned at any suitable location along the length of the tube 100 and can be constructed of any suitable size and shape. A central bar 125 is disposed at about the center of the fenestration 120 (or between a pair of such fenestrations). The central bar 125 is formed of a portion of the composite tube 100 and is integral therewith.

A separate, inner cannula 500 is slidably and removably disposed within the hollow central opening of tube 100.

A flange or mounting mechanism 200 is connected with the tracheal tube 100 in a suitable fashion. The flange is, typically, semi-rigid and radiused so that it can conform, at least partially, to the exterior of the patient's throat. In a preferred embodiment, the flange 200 is mounted to the tube 100 in any suitable fashion. For example, tube 100 and flange 200 can be integrally formed. Conversely, the two components can be formed separately and joined together in any suitable manner such as adhesives, thermal bonding or the like.

The connector 400 comprises a plurality of components. A cap 401 is threadedly attached to the proximal end of the tube 100. The connector tube 402 is mounted in the cap 401 in any suitable fashion so as to be captured therein. While not essential, in a preferred embodiment the tube 402 is swivelably mounted to the cap 401. A connector 403 of conventional design for connection to an external or respiratory system or the like is joined to the connector tube 402. Again, the tube 402 and connector 403 can be integrally formed or they can be rotatably mounted to each other in order to form a swivel connection 400. A representative connector is described in U.S. Pat. No. 5,054,482 or 5,259,376 by J. Bales.

A suitable connecting device 300 (which can also represent a source of fluid such as air or the like) is connected to the tracheal tube 100 by means of the conduit 301. The conduit 301 transfers fluid to the composite tube 100 as described infra. As noted, the component 300 can represent the source of fluid such as air or it can represent a conventional connector device which is connected to a remote source of fluid such as air.

Figure 2:
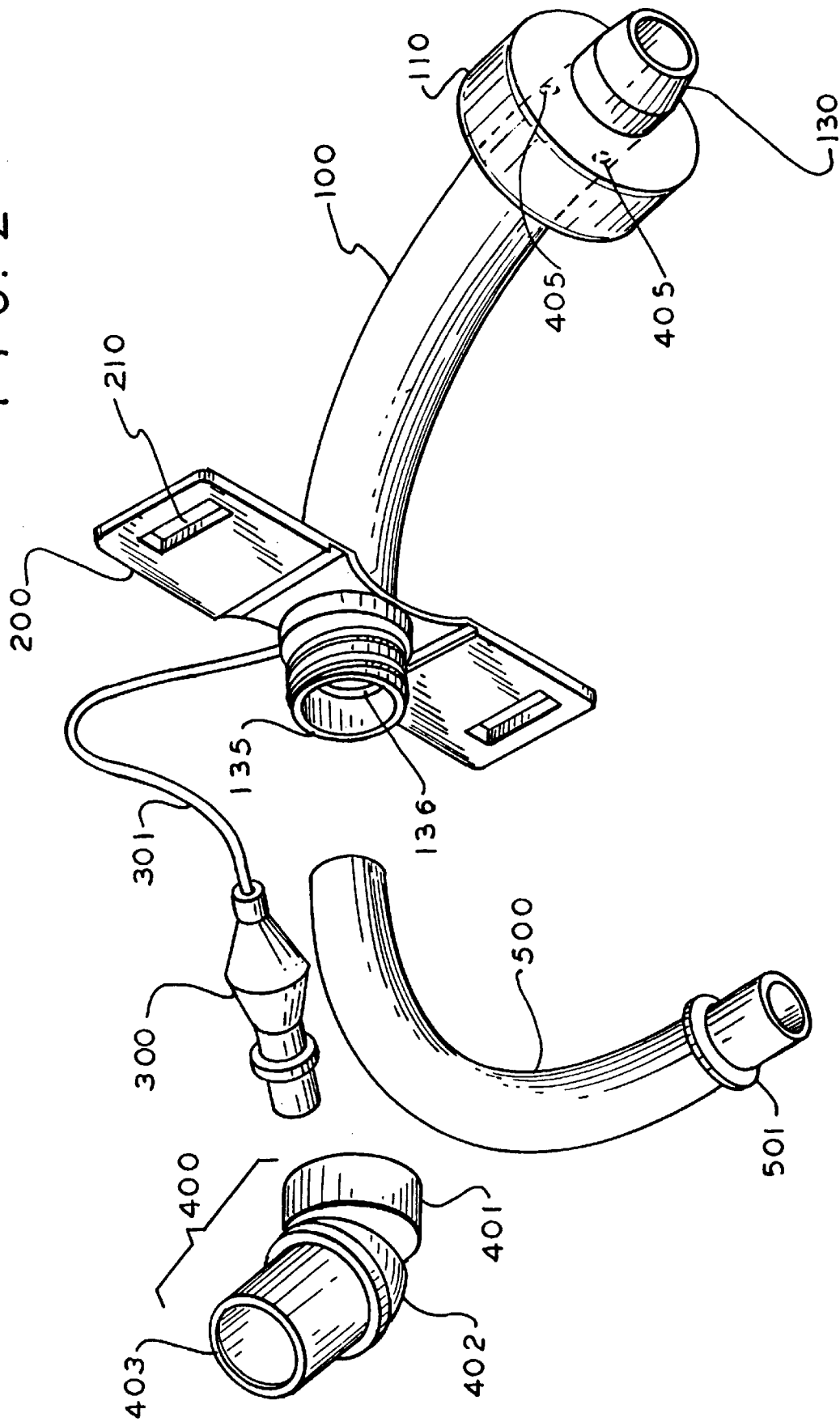
FIG. 2 is a partially exploded, oblique view of the tracheostomy tube shown in FIG. 1 including a removable inner cannula.

Referring now to FIG. 2, there is shown an oblique, partially-exploded view of the embodiment of the instant invention shown in FIG. 1 including an inner cannula 500. Also, in FIG. 2, the tracheal tube 100 has been rotated approximately 180° in order to disclose the distal end 130. In a preferred embodiment of the invention, the end 130 is rounded or tapered, as shown, in order to improve the utilization of the device and to reduce the possibility of trauma to a patient.

Again, the tracheal tube 100 is an arcuate shaped device of conventional configuration. The outer surface of the tube 100, formed of a relatively soft material, is seen to be smooth, with no exterior grooves, projections or sharp edges. The arcuate tube includes the cuff 110 shown in the inflated status as in FIG. 1. Of course, for insertion into a patient, the cuff 110 is not inflated and is substantially coplanar (or at least close to) the outer surface of the tracheal tube 100.

The tracheal tube 100 openings 120 are not shown in FIG. 2. However, one or more holes 405 (see also FIG. 4) in the tracheal tube are disposed beneath the cuff 110 in order to supply fluid to inflate the cuff. As will be seen, holes 405 pass through only the outer tube 176 of the composite tube 100. The holes 405 intersect one or more of the chambers 177 formed between the outer surface of the inner tube 175 and the inner surface of the outer tube 176. Thus, air can be supplied from source 300 to cuff 110 for inflation (or vice versa).

The flange 200 is connected with the tracheal tube 100 in a suitable fashion. In a preferred embodiment, the flange 200 includes openings 210 which are provided to engage a strap, ribbon or the like (not shown) which passes around the throat of the patient to secure the tracheostomy tube securely in place. A conventional closure cap (not shown) can be attached to the tracheostomy tube, if desired.

In FIG. 2, the proximal end 135 of the tube 100 is shown to be threaded. Cap 401 of connector 400 is adapted to be threadedly attached to the proximal end 135 of the tube 100. The connector tube 402 is mounted into the cap 401 in any suitable fashion so as to be captured therein. The conventional connector 403 is joined to the connector tube 402. Again, the tube 402 and connector 403 can be integrally formed or they can be rotatably mounted to each other in order to form a swivel connection 400.

A suitable connector 300 (or source of fluid, such as air or the like) is connected to the tracheostomy tube 100 by means of the conduit 301. As will be seen, the component 300 can represent the source of fluid, such as air, or it can represent a conventional connector device which is connected to a remote source of fluid such as air, or it can be a bellows pump or the like.

The inner cannula 500 is a relatively rigid tube, bent in substantially the same configuration as the tracheostomy tube 100 The inner cannula 500 is used, inter alia, to permit selective cleaning of the tube 100 which can become occluded during use.

The cannula 500 includes a shoulder 501 which rests upon a counterpart shoulder 136 which is provided at the interior of the proximal end 135 of tube 100 (or by the flange 200). Thus, the cannula 500 is limited in the insertion into the tube 100.

In addition, the cannula 500 includes a suitable gripping end such as a flared end or a pull ring formed at the proximal end thereof. Thus, the cannula can be removed from tube 100 as desired.

Figure 3:
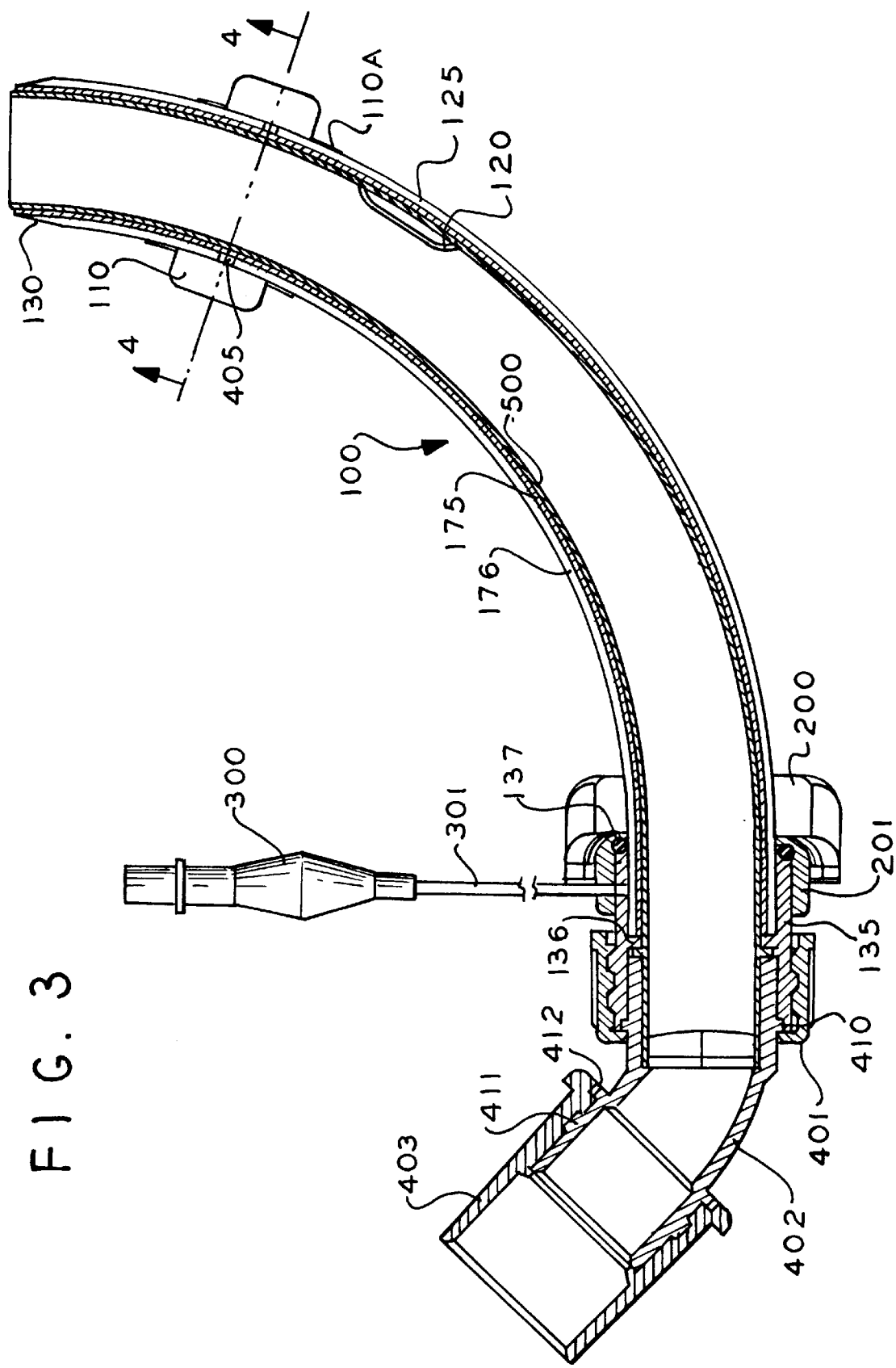
FIG. 3 is a lengthwise cross-sectional view of the tracheostomy tube of the instant invention including the removable inner cannula.

Referring now to FIG. 3, there is shown a lengthwise cross-sectional view of the embodiment of the tracheostomy tube shown in FIG. 1.

In this embodiment, the tracheostomy tube 100 comprises an arcuate shaped inner tube 175 formed of a relatively rigid material such as ABS plastic or the like which follows the conventional configuration of a tracheostomy tube. The inner tube is, typically, a rigid PVC, or the like, which has a hardness rating of about 76 Durometer (shore D).

The outer tube 176 is disposed on and surrounds the inner tube 175; accordingly, as shown in FIG. 3, it will be understood that the inner tube 175 and the outer tube 176 are coaxially nested tubes. The outer tube, typically, has a hardness rating of about 40–55 Durometer (shore A). Thus, the outer tube 176 is formed of a relatively soft material such as PVC or the like.

In one embodiment, at least one channel (see FIG. 4) is formed in the inner surface of outer tube 176. That is, tube 176 can be fabricated by an extrusion process wherein one or more channels 177 are formed. The channel (or channels) provide small airways between the inner and outer tubes when they have been assembled. One of more holes 405 pass through the soft outer tube 176 to communicate with the channels 177 as described infra.

The assembly process can, typically, comprise the steps of forming each of the inner and outer tubes, inserting the inner tube into the outer tube, bending the nested tubes to shape while heated or the like. The heating process also helps to heat shrink the outer tube 176 onto the inner tube 175 for close adherence thereto.

The arcuate tube includes a thin, substantially airtight membrane affixed thereto to form the inflatable balloon or cuff 110 (shown in the inflated status). The cuff membrane is affixed to the outer tube 176 by the edges of the membrane material. Obviously, when the cuff 110 is not inflated, it is substantially coplanar with the outer surface of the tracheal tube 100.

The tracheal tube 100 includes one or more openings 120 also known as fenestrations which pass therethrough. The bar 125 maintains a continuous internal surface for guiding the inner cannula 500. The fenestrations 120 are used for patient treatment.

The mounting mechanism, i.e. flange 200, is connected with the tracheal tube 100 in a suitable fashion. In a preferred embodiment, the flange 200 is adhered to, or integrally formed with, a connector 135 which forms the end of the tube 100. The connector 135 includes the internal shoulder 136 which limits the insertion of connector tube 402 and also forms an abutment for the end of composite tube 100. (The inner cannula 500 passes through the opening in shoulder 136.) The O-ring 137 provides an air tight seal between connector 135, flange 200 and tube 100.

The connector 134 is, typically, adhered to the end of the tube 100 but can be integrally formed therewith, if desired. Thus, the flange 200 can be joined to the end of tube 100 in any suitable fashion. For example, tube 100 and flange 200 can be integrally formed. Conversely, the two components can be formed separately and joined together in any suitable manner such as adhesive, thermal bonding or the like.

The conduit 301 from source 300 is, typically, connected through the end connector 135 into communication with one or more of the channels 177 whereby air (or other fluid) is supplied to cuff 110.

The connector cap 401 is threadedly attachable to the end connector 135 at the proximal end of the tube 100 which is also threaded. The connector tube 402 is captured in the cap 401 in any suitable fashion such as by shoulder 410 whereby the connector tube 402 is swivelably mounted to the cap 401. A connector 403 of conventional design is joined to the connector tube 402, for example, by suitable interlocking shoulders 411 and 412 whereby, the tube 402 and connector 403 can be integrally formed or they can be snapped together while rotatably mounted to each other in order to form a swivel connection 400.

Referring now to FIG. 4, there is shown a cross-sectional view of the tracheal tube 100 taken along the line 4—4 shown in FIG. 3.

In this cross-sectional view, the tracheostomy tube 100 is shown to comprise an outer tube 176 (formed of relatively soft material) and an inner tube 175 (formed of relatively hard material). The inner diameter of tube 176 and the outer diameter of tube 175 are of quite similar dimensions so as to provide an extremely snug fit between the tubes when they are mounted co-axially as shown.

As suggest supra, a plurality of striations or grooves 177 are formed in the inner surface of tube 176. These grooves form channels which extend along the length of the tracheal tube 100 as shown and described supra.

It should also be understood that it is contemplated that the grooves may be formed in the outer surface of inner tube 175, if so desired. In either case, a plurality of elongated chambers 177 are formed at the inner face between the inner and outer tubes.

At least one aperture 405 is cut, punched or otherwise formed through the outer tube 176 and interconnects with one or more grooves or conduits 177 to permit fluid flow along the respective groove. The fluid flows through the channel(s) 177 and through opening 405 under the cuff membrane 110. When sufficient fluid is supplied, for example by source 300, the cuff 110 is inflated as shown in the Figures. The cuff 110 can be deflated by withdrawing fluid by means of source (sump) 300.

As suggested supra, the inner surface of tube 176 and the outer surface of tube 175 can form a snug fit. It is also contemplated that the respective surfaces can be joined together by means of adhesive, if so desired. In addition, the respective ends of tube 100 are sealed, for example by heat treating to seal the ends of the channels 177.

Referring now to FIG. 5, there is shown an enlarged top view of the distal end of the tracheal tube 100. In this case, the cuff 110 is also shown in the inflated condition. The deflated condition of the cuff or balloon is represented by the dashed line 110B. A plurality of apertures 405 are shown in dashed outline. These apertures, as seen in FIG. 4, pass through the outer tube 176 and communicate with the channels 177 so that air can be supplied to (or removed from) cuff 110 via conduit 301.

The distal end 130 of the tracheal tube 100 is shown to be slightly tapered to enhance the utilization thereof. This tapered configuration is achieved during a heat sealing operation or a separate step of heating the assembled tracheostomy tube 100 inasmuch as the outer tube 176 (which has a much lower Durometer than the inner tube 175) shrinks in a fashion to establish this contoured end.

The fenestration 120 passes through the entire tube 100 and communicates with the open central core 600 thereof. In this embodiment, the fenestration is arranged to include a central bar 125 which is formed as part of the actual tracheostomy tube 100 and is coplanar therewith. Thus, the fenestration 120 includes an opening on either side of the central bar 125. As will be apparent, the advantage of the central bar 125 is that the distal end of the inner cannula 500 which is to be inserted into the tracheostomy tube 100 will rest upon and be guided by the central bar 125 so that the distal end of the inner cannula 500 will not engage and "hang up" on any edges of the fenestration.

Referring now to FIG. 6, there is shown an enlarged cross-sectional view of that portion of tracheostomy tube 100 which includes the fenestration 120. The fenestration 120 passes through the entire tube 100 and communicates with the open central core 600 thereof. In this embodiment, the fenestration 120 includes central bar 125 which is formed as part of the tracheostomy tube 100 so that the inner surfaces are coplanar whereby the distal end of the inner cannula 500 which is to be inserted into the tracheal tube will rest upon and be guided by this central bar as if the fenestration were not present.

Thus, there is shown and described a unique design and concept of improved tracheostomy tube with removable inner cannula. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

What is claimed is:

1. A tracheostomy tube comprising, inner and outer coaxially nested tubes, said inner tube formed of a first material which retains a particular configuration when so formed, said outer tube formed of a second material which conforms to the configuration of said inner tube, said second material being softer than said first material, at least one opening through said inner and outer tubes, and a central bar in said one opening which bar is substantially co-planar with said inner and outer tubes.

2. The tracheostomy tube recited in claim 1 including, at least one channel formed between said inner and outer tubes.

3. The tracheostomy tube recited in claim 1 including, at least one opening through said outer tube to communicate with said channel between said inner and outer tubes.

4. The tracheostomy tube recited in claim 3 including, a membrane mounted on said outer tube over said opening in said outer tube.

5. The tracheostomy tube recited in claim 1 including, a flange connected to one end of said tracheostomy tube for selectively mounting said tube to a patient.

6. The tracheostomy tube recited in claim 1 including,
a connector for connecting said tracheostomy tube to an external respiratory system.

7. The tracheostomy tube recited in claim 1 including,
an end connector for connecting one end of said tracheostomy tube to said connector.

8. The tracheostomy tube recited in claim 1 including,
fluid supply means connected to said tracheostomy tube.

9. The tracheostomy tube recited in claim 1 including,
an inner cannula which is conformed to be removably inserted within said tracheostomy tube.

10. A tracheostomy tube comprising,
inner and outer coaxially nested tubes;
said inner tube formed of a first material which retains a particular configuration when so formed,
said outer tube formed of a second material which conforms to the configuration of said inner tube, said second material being softer than said first material,
at least one channel formed between said inner and outer tubes to selectively pass fluid therethrough,
a first opening through said inner and outer tubes,
a second opening through said outer tube to communicate with said channel between said inner and outer tubes, and
a membrane mounted on said outer tube over said second opening in said outer tube whereby said membrane can be selectively inflated by fluid passing through said channel.

11. The tracheostomy tube recited in claim 10 wherein,
said at least one channel is axially formed between said inner and outer tubes.

12. The tracheostomy tube recited in claim 10 including,
a central bar in said first opening which bar is coplanar with said inner tube.

13. The tracheostomy tube recited in claim 10 including,
a flange connected to one end of said tracheostomy tube for selectively mounting said tracheostomy tube to a patient.

14. The tracheostomy tube recited in claim 10 including,
fluid supply means connected to selectively supply fluid to said channel.

15. The tube recited in claim 10 including,
an inner cannula which is conformed to be removably inserted with said tube.

16. A tracheostomy tube comprising,
inner and outer coaxially nested tubes of substantially constant diameters,
said inner tube formed of a first material which retains a particular configuration when so formed, said outer tube formed of a second material which snugly conforms to the configuration of said inner tube, said second material being softer than said first material,
at least one channel disposed between said inner and outer tubes, and
a sealed end of said inner and outer tubes which is contoured to provide a relatively soft distal end therefor.

17. The tracheostomy tube recited in claim 16 including,
at least one opening through said outer tube to communicate with said channel between said inner and outer tubes.

18. The tracheostomy tube recited in claim 17 including,
a membrane mounted on said outer tube over said opening in said outer tube.

19. The tracheostomy tube recited in claim 16 including,
a connector for connecting said tracheostomy tube to an external respiratory system.

20. The tracheostomy tube recited in claim 19 including,
an end connector for connecting one end of said tracheostomy tube to said connector.

* * * * *